United States Patent [19]

Heimerl et al.

[11] Patent Number: 5,176,306
[45] Date of Patent: Jan. 5, 1993

[54] INSTRUMENT FOR SETTING WOUND CLAMPS

[75] Inventors: Albert Heimerl; Holger Kartheus, both of Hamburg; Dietmar Paske, Buxtehude; Hans-Ulrich Plenio, Hamburg, all of Fed. Rep. of Germany

[73] Assignee: Beiersdorf AG, Hamburg, Fed. Rep. of Germany

[21] Appl. No.: 834,608

[22] Filed: Feb. 12, 1992

[30] Foreign Application Priority Data

Mar. 19, 1991 [DE] Fed. Rep. of Germany ....... 4108952

[51] Int. Cl.$^5$ ...................... A61B 17/068; B25C 5/02
[52] U.S. Cl. ..................................... 227/176; 227/19
[58] Field of Search ................. 227/19, 175, 176, 177, 227/120

[56] References Cited

U.S. PATENT DOCUMENTS

| | | |
|---|---|---|
| 2,874,384 | 2/1959 | Krone .................................. 227/19 |
| 3,873,016 | 3/1975 | Fishbein .............................. 227/19 |
| 4,109,844 | 8/1978 | Becht .................................. 227/19 |
| 4,375,866 | 3/1983 | Giersch et al. ..................... 227/19 |
| 4,411,378 | 10/1983 | Warman ............................. 227/19 |
| 4,813,586 | 3/1989 | Seifert ................................ 227/19 |
| 5,080,275 | 1/1992 | Heimerl et al. ................... 227/176 |

Primary Examiner—Frank T. Yost
Assistant Examiner—Scott A. Smith
Attorney, Agent, or Firm—Dvorak and Traub

[57] ABSTRACT

An instrument for setting wound clamps consists of first and second parts detachably connected by means of a first connection. The first part, which is a disposable part, receives a magazine containing wound clamps, and tools for deforming and implanting the wound clamps. The second part has handles for operating the tools. When the instrument is being operated, forces are generated which may cause the two parts of the instrument to become separated. A second connection between the two parts of the instrument, which connection is only effective during the operation of the instrument is, therefore, provided.

8 Claims, 2 Drawing Sheets 025,176,306

INSTRUMENT FOR SETTING WOUND CLAMPS

FIELD OF THE INVENTION

This invention relates to an instrument for setting wound clamps, the instrument comprising a first part having means for setting wound clamps contained in a magazine, and a second part having a fixed handle and a handle which is movable with respect to the fixed handle for operating said setting means.

BACKGROUND OF THE INVENTION

With the increasing use of wound clamp setting instruments instead of conventional suturing by means of needle and thread, for closing wounds, the cost of closing wounds has correspondingly increased, so that the costs of manufacture and subsequent use of wound clamp setting instruments needs to be kept low. Conventional disposable wound clamp setting instruments, which cannot be re-used after sterilisation do not meet this need. It has, therefore, been proposed to construct only part of a wound clamp setting instrument as a disposable part. According to DE-A-3 934 698 such an instrument consists of a first part comprising a magazine receiving wound clamps, which part cannot be re-used, and a second part comprising handles and other parts which can be re-used after being sterilised. This approach to the manufacture of wound clamp setting instruments, reduces the costs mentioned above and is also environment friendly.

Where the instrument is made in two parts as described above, the parts must be easily connectable and detachable by the operator, for example when the magazine is to be changed during an operation. The connection between the two parts must, however, be secure whilst the instrument is in use in a wound closing operation.

It has been found that a conventional stop-connection or snap-connection between the two parts of the instrument has a holding power which is sufficient only to maintain the connection between the two parts when the instrument is at rest, rather than during its use in a wound closing operation. During such use, closure of the handles generates forces acting on the magazine, the tools for setting the wound clamps and other components of the instrument, which forces may be such as to overcome a conventional connection between the two parts of the instrument so that they are unintentionally separated.

SUMMARY OF THE INVENTION

The present invention is intended to provide an instrument for setting wound clamps in which the two parts of the instrument can be connected and disconnected with the expenditure of little force when the instrument is not in use in a wound closing operation, but in which the connection between the parts cannot be broken while such an operation is in progress.

According to the present invention, therefore, a further connection between the two parts of the instrument is provided which is effective only when the instrument is being operated to close a wound.

Said further connection provides a holding force which is additional to that of the first connection which may comprise, for example, a snap mechanism, the further connection being inoperative when the instrument is not in use in closing a wound.

By suitable functional and structural design of said further connection it can be achieved that the two parts of the instrument cannot become detached from each other during a wound closing operation. Thus, the first or snap connection need only provide sufficient holding force to prevent disconnection of the two parts of the instrument when it is not in use so that said forces tending to separate said two parts are not present. The second connection may be such as to provide temporarily effective positive locking between said two parts. The components of such a positive locking arrangement preferably extend about the axis of rotation of the movable handle, being disposed, on the one hand of the movable handle and on the other hand on a part of the instrument which is fixed relative to the movable handle. When the movable handle is constituted by a longer arm of a two armed lever, the other arm of which acts upon a tool for setting the clamps, the components of the positive locking arrangement may be disposed on a shorter arm and on said first part of the instrument, carrying the magazine. In this case the said components may be provided on two opposite lateral sides of said shorter arm and on two opposite side walls of a housing of said first part of the instrument.

A positive connection between the two parts of the instrument, which connection is only operative when the tool is in use in a wound closing operation, can also be produced by arranging for said two parts to be arrested, locked, or hooked to each other by a pin, bolt, or hook which is adjustable by actuation of the handles. Force-locking connections with clamping or spreading elements may also be used for this purpose.

DETAILED DESCRIPTION OF A PREFERRED EMBODIMENT OF THE INVENTION

Figure 1:
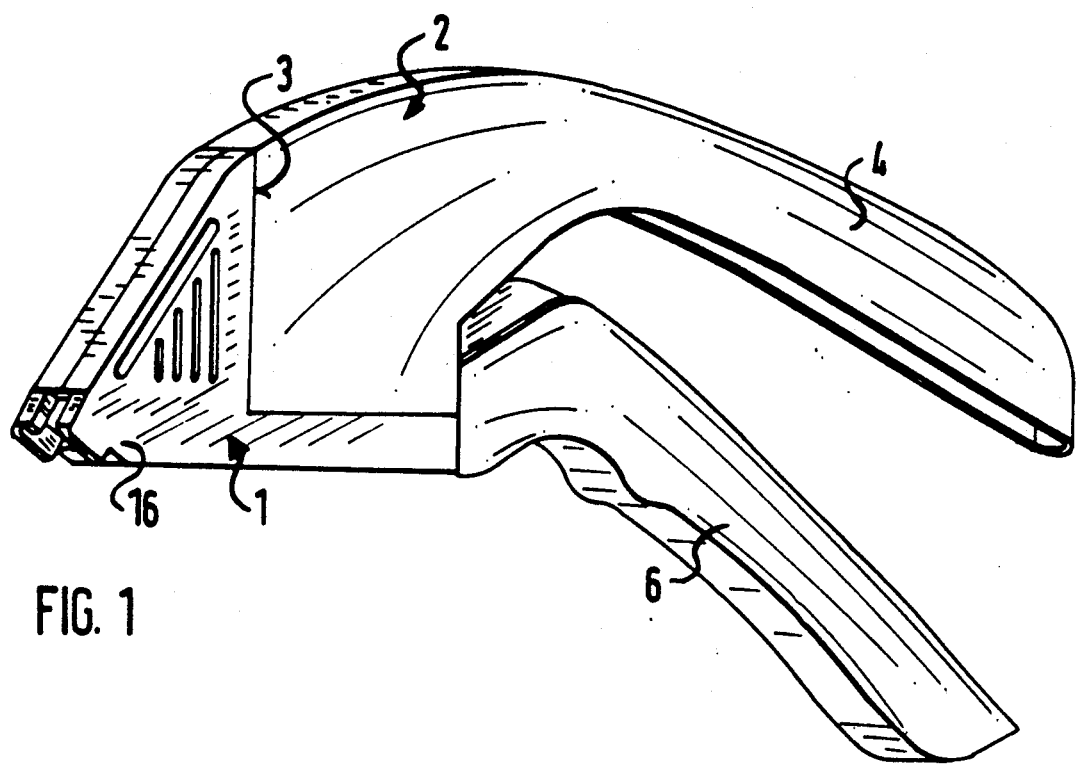
FIG. 1 is an isometric side view of an instrument according to the present invention, for setting wound clamps.

An instrument for setting wound clamps comprises detachably connectable first and second parts 1 and 2, respectively, which when connected abut each other along a junction plane 3. The first part 1, which is a disposable part, accommodates therein wound clamps held in a magazine (not shown), tools 8 (shown partially) for deforming and implanting the wound clamps, and other parts (not shown) which are disclosed in EP-A-0 244 854, WO-A-82/02 486 and U.S. Pat. No. 4 109 844, all three of which documents are hereby incorporated herein by reference.

The second part 2, which is intended to be sterilised after use, comprises a fixed handle 4 and a handle 6 which is movable relatively towards and away from the fixed handle 4 about a swivel axis 5. The handle 6, which is disposed on one side of the axis 5, and a lever arm 7 which is shorter than the handle 6 and is disposed on the opposite side of the axis 5, constitute a two armed lever. The free end of the arm 7 is actuable by means of the handle 6 act upon the tools 8 to hold and deform the wound clamps during use of the instrument 1,2.

The first part 1 of the instrument has a housing provided with an extension 9 having a depending nose 10, which upon the parts 1 and 2 of the instrument being assembled together snaps into a recess 11 in a wall 12 of an opening in a mounting 13 on the part 2, which opening receives the extension 9. The snap connection provided by the nose 10 and recess 11 constitutes a releasable first connection between the parts 1 and 2 of the wound clamp setting instrument. Instead of the snap connection 10, 11, some equivalent connection which is operable automatically when connecting and disconnecting the parts 1 and 2, may be provided.

When, during operation of the instrument 1, 2, the handle 6 is pressed towards the handle 4 so that the lever arm 7 causes the tools 8 to act upon a wound clamp, the considerable forces generated at the site of such action result in correspondingly high loading of the snap connection 10, 11, which may be released by reason of the shearing and tilting forces to which it is subjected. In order to prevent the parts 1 and 2, so becoming separated when the instrument is being operated, there is accordingly provided a second connection between these parts which only becomes effective during operation of the instrument. An embodiment of this second connection will now be described.

Figure 3:
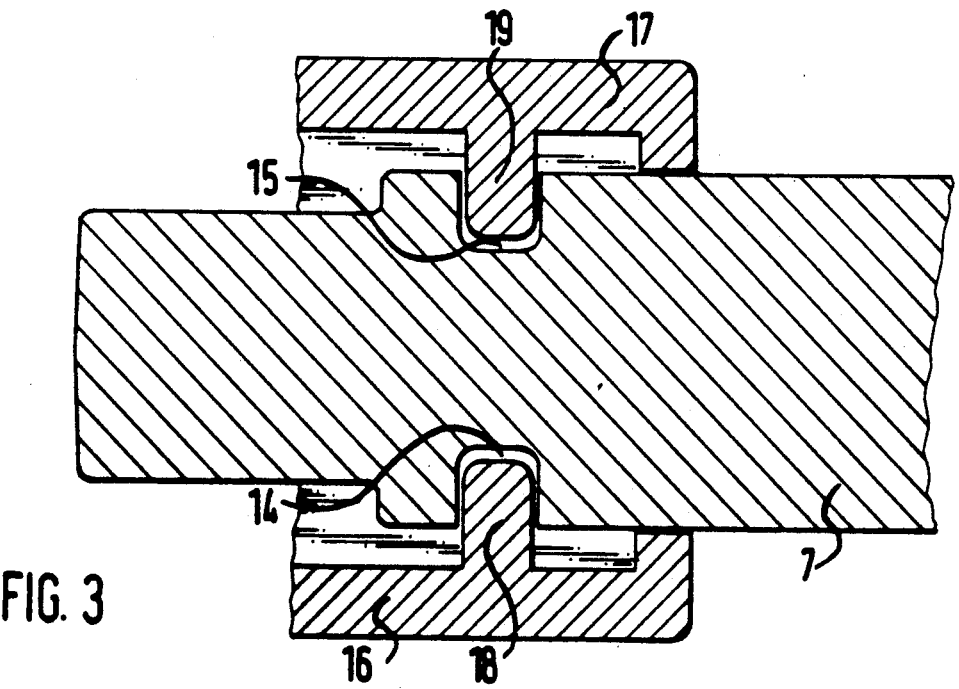
FIG. 3 is a sectional view taken on the lines III—III in FIG. 2.
Figure 2:
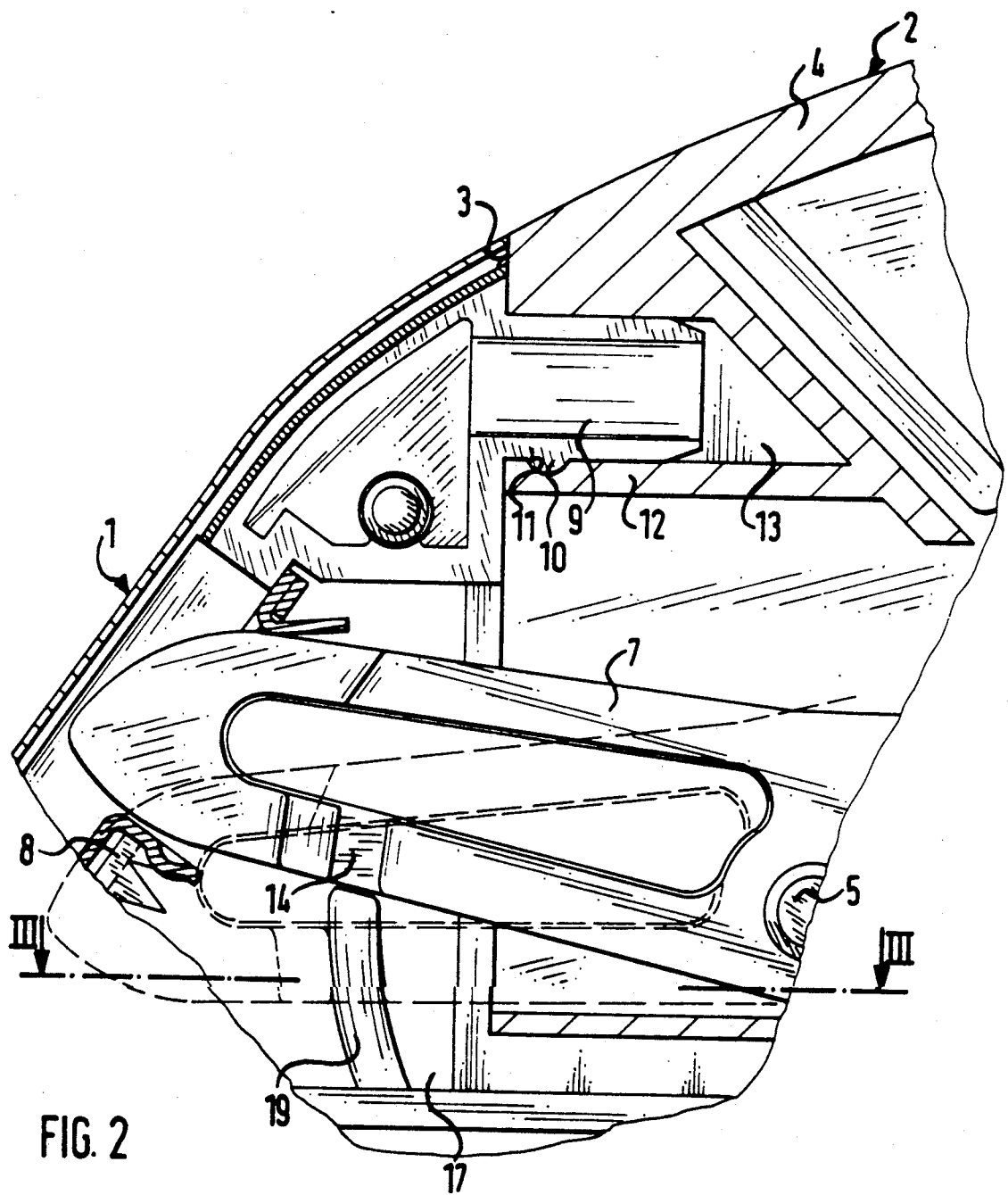
FIG. 2 is a fragmentary longitudinal sectional view of the instrument.

As shown in FIGS. 2 and 3 there are provided on opposite vertical sides of the lever arm 7 recesses 14 and 15, respectively, there also being provided in two opposite walls 16 and 17 of the first part 1 of the wound clamp setting instrument, projections 18 and 19 each extending along a circular arc, these arcs being of equal radius, about the axis 5. The recesses 14 and 15 also extend along said arcs.

The arm 7 is shown in FIGS. 2 in full lines in the angular position that it occupies when the instrument is not being operated, that is to say when the tool is at rest. As the handle 6 is being pressed towards the handle 4 to operate the instrument, the arm 7 is depressed, so that the projections 18 and 19 engage in the recesses 14 and 15, respectively, in the manner of a tongue and groove connection. As the operation of the instrument progresses the arm 7 is further depressed so that the projections 18 and 19 engage further into, and through, the recesses 14 and 15, as shown in FIG. 3, until the lever arm 7 has carried out its working stroke and so has reached its end angular position indicated in broken lines in FIG. 2.

The engagement of the projections 18 and 19 in the recesses 14 and 15 creates a positive mechanical connection between the parts 1 and 2 of the instrument which holds them together during its operation, said positive connection being automatically released as soon as the handle 6 is relieved of load after the implantation of the wound clamp, so as to be returned to its position of rest, the lever arm 7 having accordingly been returned to its starting position shown in full lines in FIG. 2. Since the projections 18 and 19 have now been withdrawn from the recesses 14 and 15, the parts 1 and 2 of the instrument can be separated from each other as required, unimpeded by said second connection, said first connection, between the nose 10 and recess 11, being easily released by pulling the parts 1 and 2 of the instrument apart.

What is claimed is:

1. An instrument for setting wound clamps, the instrument comprising:
    a first part comprising a magazine for carrying wound clamps and means for setting the wound clamps contained in said magazine;
    a second par comprising a fixed handle and a movable handle which is movable with respect to said fixed handle for operating said setting means;
    first connecting means having engageable portions on said first and second parts for detachably interconnecting said first and second parts together in operative relationship; and
    second connecting means comprising spaced apart members on both said first and second parts, said spaced apart members being effective to connect said first and second parts together only during the setting of the wound clamps.

2. An instrument as claimed in claim 1, wherein said second connecting means comprises means on said first and second parts for positively locking said first and second parts together.

3. An instrument as claimed in claim 1, wherein said movable handle is movable with respect to said fixed handle about a swivel axis, said second connecting means comprising means spaced from said axis and pivotable about said axis for positively locking said parts of the instrument together.

4. An instrument as claimed in claim 1, wherein said movable handle constitutes a longer arm of a two armed lever, a shorter arm of said lever being engageable with tooling for implanting said clamps, said second connection means comprising means on said shorter arm and said first part of the instrument, for positively locking said first and second parts of said instrument together.

5. An instrument as claimed in claim 4, wherein said positive locking means are provided on longitudinally extending lateral surfaces of said shorter arm and on opposite side walls of said first part of the housing.

6. An instrument as claimed in claim 1, wherein said second connecting means comprises means for positively locking said first and second parts together.

7. An instrument as claimed in claim 1, wherein said first connecting means comprises snap connection means for acting between said two parts of the instrument.

8. An instrument as claimed in claim 7, wherein said first connecting means comprises an extension on said first part of the instrument and a mounting for said extension on said second part of the instrument, said snap connection means being provided on said extension and said mounting.

* * * * *